(12) United States Patent
Kato (10) Patent No.: US 6,822,096 B2
(45) Date of Patent: Nov. 23, 2004

(54) ENVIRONMENT-SENSITIVE LUMINESCENT DIMINE-PLATINUM BINUCLEAR COMPLEXES

(75) Inventor: Masako Kato, Nara (JP)

(73) Assignee: Japan Science and Technology Agency, Saitama (JP)

(*) Notice: Subject to any disclaimer, the term of this patent is extended or adjusted under 35 U.S.C. 154(b) by 0 days.

(21) Appl. No.: 10/476,617

(22) PCT Filed: Jun. 5, 2002

(86) PCT No.: PCT/JP02/05529

§ 371 (c)(1),
(2), (4) Date: Nov. 3, 2003

(87) PCT Pub. No.: WO03/018558

PCT Pub. Date: Mar. 6, 2003

(65) Prior Publication Data

US 2004/0138456 A1 Jul. 15, 2004

(30) Foreign Application Priority Data

Aug. 23, 2001 (JP) ........................ 2001-253550

(51) Int. Cl.[7] .......................... C07F 15/00; G01N 31/00
(52) U.S. Cl. .............................. 546/2; 556/137; 436/2; 436/164; 436/805
(58) Field of Search .................... 436/2, 164, 805; 546/2; 556/137

(56) References Cited

U.S. PATENT DOCUMENTS

| 4,826,774 A | 5/1989 | Nagel .......................... 436/106 |
| 5,445,785 A | 8/1995 | Rhim .......................... 264/555 |

FOREIGN PATENT DOCUMENTS

| JP | 1-221484 A1 | 9/1989 |
| JP | 5-279942 A1 | 10/1993 |

OTHER PUBLICATIONS

Tzeng et al."Structures and photoluminescence of dinculear platinum(II) and palladium(II) complexes with bridging thiolates and 2,2'–bipyridine or 2,2':6',2"–terpyridine ligands," J. Chem. Soc., Dalton Transactions, pp. 1017–1023 (1999).

Kato et al., "Vapor–induced luminescence switching in crystals of the Syn Isomer of a dinuclear (Bipyridine)platinum(II) complex bridged with pyridine–2–thiolate ions," Angewandte Chemie, vol. 41, No. 17, pp. 3183–3185, Wiley–VCH Veral GmbH & Co. (2002).

International Search Report (English Translation).

*Primary Examiner*—Porfirio Nazario-Gonzalez
(74) *Attorney, Agent, or Firm*—Rader, Fishman & Grauer PLLC (57) ABSTRACT

Chemicals which make not only a dark-red/light-red change of color but also a near-infrared/red change of luminescence via reversible adsorption/desorption of vapor of acetonitrile or ethanol, and therefore permit the observation of on-off change of visually effective luminescence and thus are useful as highly sensitive sensors. The chemicals are binuclear platinum (II) complexes of the following general formula: $[Pt_2(L)_2(bpy)_2]X_2$ or $[Pt_2(L)_2(bpy)_2]Y$ (wherein L is a bridging ligand selected from among 2-pyridinethiol anion, 2-quinolinethiol anion, 8-quinolinethiol anion and so on; bpy is 2,2-bipyridine; X is a monovalent anion; and Y is a bivalent anion), characterized by taking a syn form wherein the two bridging ligands (L) coordinate to one platinum ion at their respective sulfur atoms and to the other platinum ion at their respective nitrogen atoms.

18 Claims, 7 Drawing Sheets

ENVIRONMENT-SENSITIVE LUMINESCENT DIMINE-PLATINUM BINUCLEAR COMPLEXES

TECHNICAL FIELD

The present invention relates to binuclear platinum (II) complexes which respond to organic molecular gas (vapor) in the environment to exhibit color changes and luminescent changes.

BACKGROUND ART

Major patent references for compounds having a vapochromic nature where the compound responds to organic molecular gas (vapor) to exhibit color and luminescent changes include the followings.

(1) U.S. Pat. No. 4,826,774 (Nagel, 1989, Vapochromic double-complex salts)

Summary: It is made of a transit metallic double-complex salt containing arenylisonitrile ligand induced with long aliphatic hydrocarbon chains, its cation is tetrakis isonitrile platinum ion and its anion is tetracyanopalladium ion. These binuclear salts exhibit new vapochromic effects and are useful as a personal badge monitor, limit monitor, optic sensor, chemical field effect transistor and related monitor application articles.

(2) U.S. Pat. No. 5,445,785 (Lancaster et al., 1995, Volatile organic compound sensing devices)

Summary: Apparatus using a vapochromic substance having a composition of an inorganic double-complex salt of which color is changed reversibly when exposed to volatile organic compound (VOC) vapors is applied for the detection of VOC vapor, detection of VOC aqueous medium, and selective detection of VOC vapor. A fundamental VOC vapochromic sensor is incorporated in various devices such as a ground probe sensor, wrist band sensor, periodic sampling monitor, soil penetrometer, evaporation purge sensor, and various vacuum-based sensors. In particular, they are applied for reversible and recyclable detection, remote detection, continuous monitoring or rapid screening in the environmental improvement and waste disposal plants. Vapochromic sensors are used in combination with various fiber optic configurations since they give a presence indication of VOC with a presence correction of VOC qualitatively and quantitatively.

(3) U.S. Pat. No. 5,766,952 (Mann et al., 1998, Vapochromic platinum-complexes and salts)

Summary: This invention relates to the following processes: indicating the presence of an organic matter vapor including a stage to determine an absorption spectrum or luminescent spectrum of platinum-platinum double complex salt or neutral platinum complex in the absence of an organic vapor; exposing the above platinum-platinum double complex salt or neutral platinum complex to an gaseous environment; and the exposure to the above gaseous environment followed by determining color, the absorption spectrum or luminescent spectrum of the above platinum-platinum double complex salt or neutral platinum complex.

The double complexes are represented by the following general chemical formulae: [Pt(CN—$C_6H_4$—R)$_4$][PtX$_4$], [Pt(phen)(CN—$C_6H_4$—R)$_2$][PtX$_4$], [Pt(bpy)(CN—$C_6H_4$—R)$_2$][PtX$_4$], [Pt(CN—$C_6H_4$—$C_nH_{2n+1}$)$_4$][Pt(CN)$_4$], [Pt(phen)(CN—$C_6H_4$—R)$_2$][Pt(CN)$_4$], [Pt(bpy)(CN—$C_6H_4$—R$_2$)][Pt(CN)$_4$]; n is an integer between 1 and 100, usually n=1 to 20; phen is 1,10-phenanthroline or alkyl substituted 1,10-phenanthroline; bpy is 2,2'-bipyridine or alkyl substituted 2,2'-bipyridine; [PtX$_4$]$^{2-}$ can be [Pt(NO$_2$)$_4$]$^{2-}$, [Pt(Cl)$_4$]$^{2-}$, [PtBr$_4$]$^{2-}$, [Pt(NCO)$_4$]$^{2-}$, [Pt(NCS)$_4$]$^{2-}$, and [Pt(oxalate)$_4$]$^{2-}$; and palladium analogues of [PtX$_4$]$^{2-}$ are allowed in bpy and phen complexes. The neutral complexes are [Pt(CN—$C_6H_4$—R)$_2$X$_2$], and [Pt(CN—$C_6H_4$—R)(C(Y)=NH—$C_6H_4$—R)X$_2$]; n is a positive integer between 1 and 100; Y is more preferably O-alkyl, NH-alkyl, and N(alkyl)$_2$, with n=1 to 20, X=CN$^-$, but the other negatively charged groups (NO$_2^-$, NCO$^-$, NCS$^-$, Cl$^-$, Br$^-$, I$^-$, ox, etc.) can be used. One X$^-$ group is not necessarily identical.

DISCLOSURE OF THE INVENTION

The objective of the invention is to provide chemicals which make not only a dark-red/light-red change of color but also a near-infrared/red change of luminescence via reversible absorption/desorption of vapor of acetonitrile or ethanol, and therefore permit the observation of on-off change of visually effective luminescence and thus can become highly sensitive sensors.

The present invention relates to a binuclear platinum (II) complex represented by the following formula:

[Pt$_2$(L)$_2$(bpy)$_2$]X$_2$ or [Pt$_2$(L)$_2$(bpy)$_2$]Y (wherein L represents a bridging ligand, as well as bpy represents 2,2'-bipyridine, X and Y represent a monovalent anion and bivalent anion, respectively), characterized in that both of the two bridging ligands are coordinated to one platinum ion by S and to the other platinum ion by N(syn isomer).

The invention further relates to a method for producing the binuclear platinum (II) complex described in claim 1, comprised by adding [PtCl$_2$(bpy)$_2$] and an equivalent amount of the bridging ligand (L) to water, heating the suspension, filtrating the impurity, subsequently adding an excess salt compound containing X or Y, for example, adding an excess NH$_4$PF$_6$ to the resultant solution to generate precipitate, obtaining the precipitate by filtration and recrystallizing from an organic solvent.

The binuclear platinum (II) complex of the invention is structurally characterized in the syn type where two bridging ligands are coordinated to one platinum ion by S and to the other platinum ion by N.

Such structural characteristic can specifically and reversibly absorb and desorbe vapor of organic molecules such as acetonitrile, alcohols such as ethanol, and methylene chloride, and cause the color change between dark-red and light-red and simultaneously induce near-infrared/red change of luminescence, and therefore observe on-off of visually effective luminescence. Incidentally, the binuclear platinum (II) complex of the invention exhibits no change for water and chloroform.

Therefore, the present invention also relates to an organic molecular detection sensor comprising the above binuclear platinum (II) complex, and an organic molecular vapor monitor apparatus including the detection sensor by taking advantage of such a nature of the binuclear platinum (II) complex.

Further, the present invention also relates to a method for detecting volatile organic molecules in the environment by taking advantage of the color change of the above binuclear platinum (II) complex, and a method for detecting volatile organic molecules in the environment by taking advantage of the luminescent change of the above binuclear platinum (II) complex.

BEST MODE FOR CARRYING OUT THE INVENTION

In the binuclear platinum (II) complex of the invention, X which is a monovalent anion and Y which is a bivalent anion are given anions typically used as counterions in the art, but a suitable example of X is selected from the group consisting of PF$_6^-$, ClO$_4^-$, BF$_4^-$, Cl$^-$ and Br$^-$, and a suitable example of Y can include SO$_4^{2-}$.

A suitable example of the bridging ligand (L) can include thiolate anions derived from heterocyclic aromatic compounds such as pyridine, quinoline and derivatives thereof, in particular, a compound selected from the group consisting of pyridine-2-thiolate anion (pyt), qionoline-2-thiolate anion (2-qlt) and quinoline-8-thiolate anion (8-qlt). Here, two bridging ligands (L) may be the same compounds or different compounds one another.

The binuclear platinum (II) complex of the invention can be produced, for example, by adding [PtCl$_2$(bpy)$_2$] and the equivalent bridging ligand (L) to water, heating the suspension, filtrating the impurity, subsequently adding an excess salt compound containing X or Y, for example, an excess NH$_4$PF$_6$ to the resultant solution to generate precipitate, obtaining the precipitate by filtration and recrystallizing from an organic solvent.

Reaction conditions such as temperature and reaction time when the suspension containing [PtCl$_2$(bpy)$_2$] and the bridging ligand (L) is heated can be selected by those skilled in the art depending on the type of the bridging ligand (L) and so on. Typically, it is heated at a temperature of, for example, 50 to 70° C. for 17 to 24 hours. Also, the organic solvents can include, for example, acetonitrile, ethanol, and a mixture of acetonitrile and ethanol and the like. Here, any of the compounds has high solubility for acetonitrile and lower solubility for ethanol, and thus, precipitation of the crystal can be controlled by appropriately mixing them.

EXAMPLES

The present invention is more specifically illustrated below by examples, but the invention is not limited to these examples.

Example 1

Synthesis and Natures of [Pt$_2$(L)$_2$(bpy)$_2$](PF$_6$)$_2$

[PtCl$_2$(bpy)$_2$] (Morgan, G. T. and Burstall, F. H., J. Chem. Soc., 1934:965) and an equivalent amount of L (pyridine-2-thiolate anion (pyt), qionoline-2-thiolate anion (2-qlt) or quinoline-8-thiolate anion (8-qlt)) were added to water, and the suspension was heated at 50° C. for 17 hours. The yellow impurity was filtrated, subsequently an excess of NH$_4$PF$_6$ was added to the resultant black brown solution, and then red precipitate was generated. The precipitate was obtained by filtration and recrystallized from acetonitrile-ethanol to yield orange needlelike crystal and red black polyhedral crystal.

Values of Elemental Analysis

[Pt$_2$(pyt)$_2$(bpy)$_2$](PF$_6$)$_2$; calculated (Pt$_2$C$_{30}$H$_{24}$N$_6$S$_2$P$_2$F$_{12}$) C 29.71, H 1.99, N 6.93%; observed C 29.58, H 2.22, N 7.13%. [Pt$_2$(8-qlt)$_2$(bpy)$_2$](PF$_6$)$_2$·0.5CH$_3$CN; calculated (Pt$_2$C$_{39}$H$_{29.5}$N$_{6.5}$S$_2$P$_2$F$_{12}$) C 35.13, H 2.23, N 6.83%; observed C 35.18, H 2.59, N 6.53%. [Pt$_2$(2-qlt)$_2$(bpy)$_2$](PF$_6$)$_2$; calculated (Pt$_2$C$_{38}$H$_{28}$N$_6$S$_2$P$_2$F$_{12}$) C 34.76, H 2.15, N 6.40%; observed C 34.74, H 2.24, N 6.49%.

Figure 1:
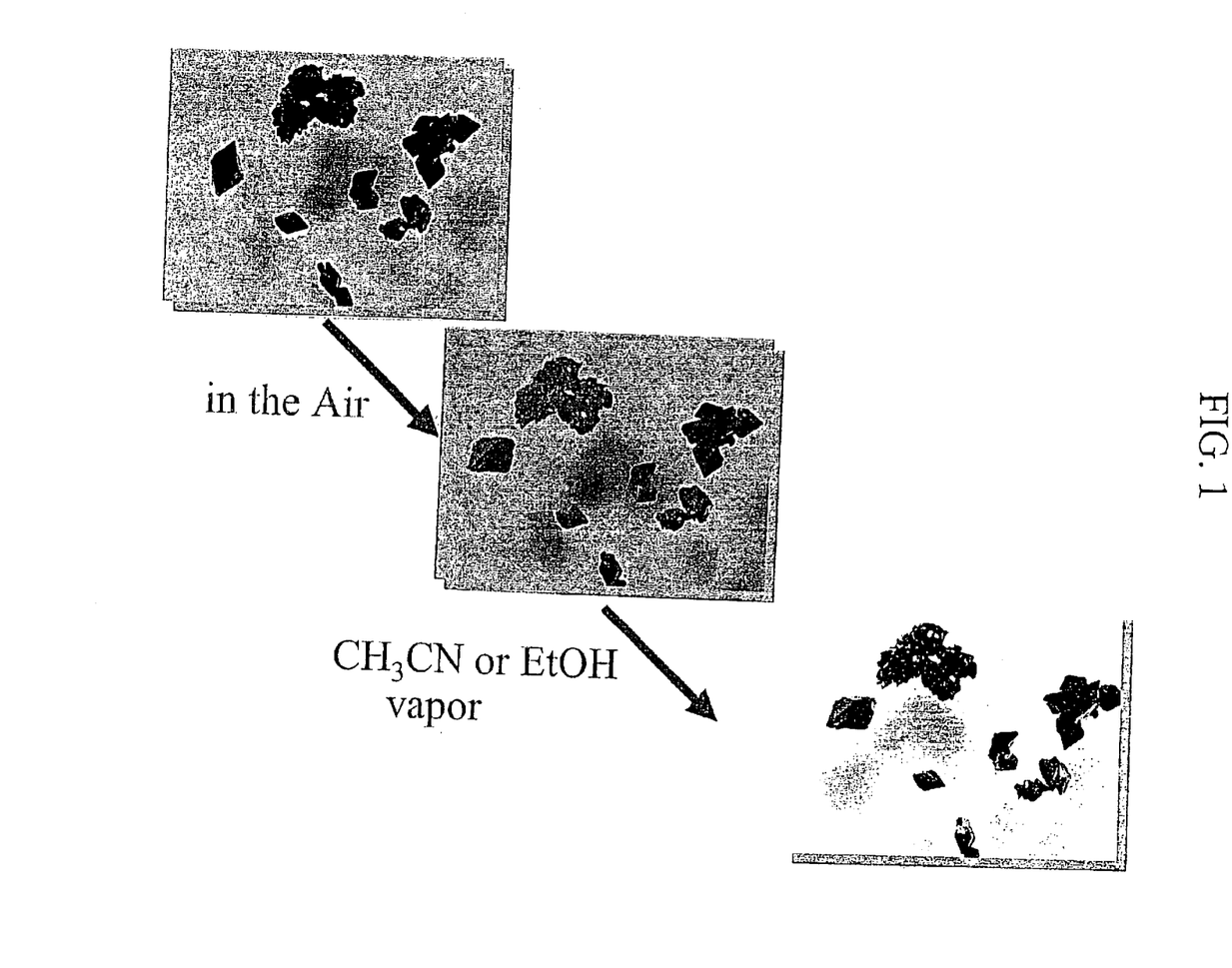
FIG. 1 is photographic images of crystals of the syn isomer of [Pt$_2$(pyt)$_2$(bpy)$_2$](PF$_6$)$_2$ illustrating vapochromic effects.

Vapochromic Behavior of [Pt$_2$(pyt)$_2$(bpy)$_2$](PF$_6$)$_2$ Red Black Polyhedral Crystal Upon standing in the air, [Pt$_2$(pyt)$_2$(bpy)$_2$](PF$_6$)$_2$ red black polyhedral crystal gradually changed to red in color. This occurs by desorbing acetonitrile of the solvent molecules contained in the crystal. Conversely, when the red crystal with desorbed solvent molecules is exposed to the organic vapor such as acetonitrile and ethanol, it immediately changes to red black in color and can not be distinguished from the original red black polyhedral crystal in appearance (FIG. 1). Thus, the [Pt$_2$(pyt)$_2$(bpy)$_2$](PF$_6$)$_2$ red black polyhedral crystal exhibits the reversible change of black and red in highly sensitive response to volatile organic molecules.

Figure 2:
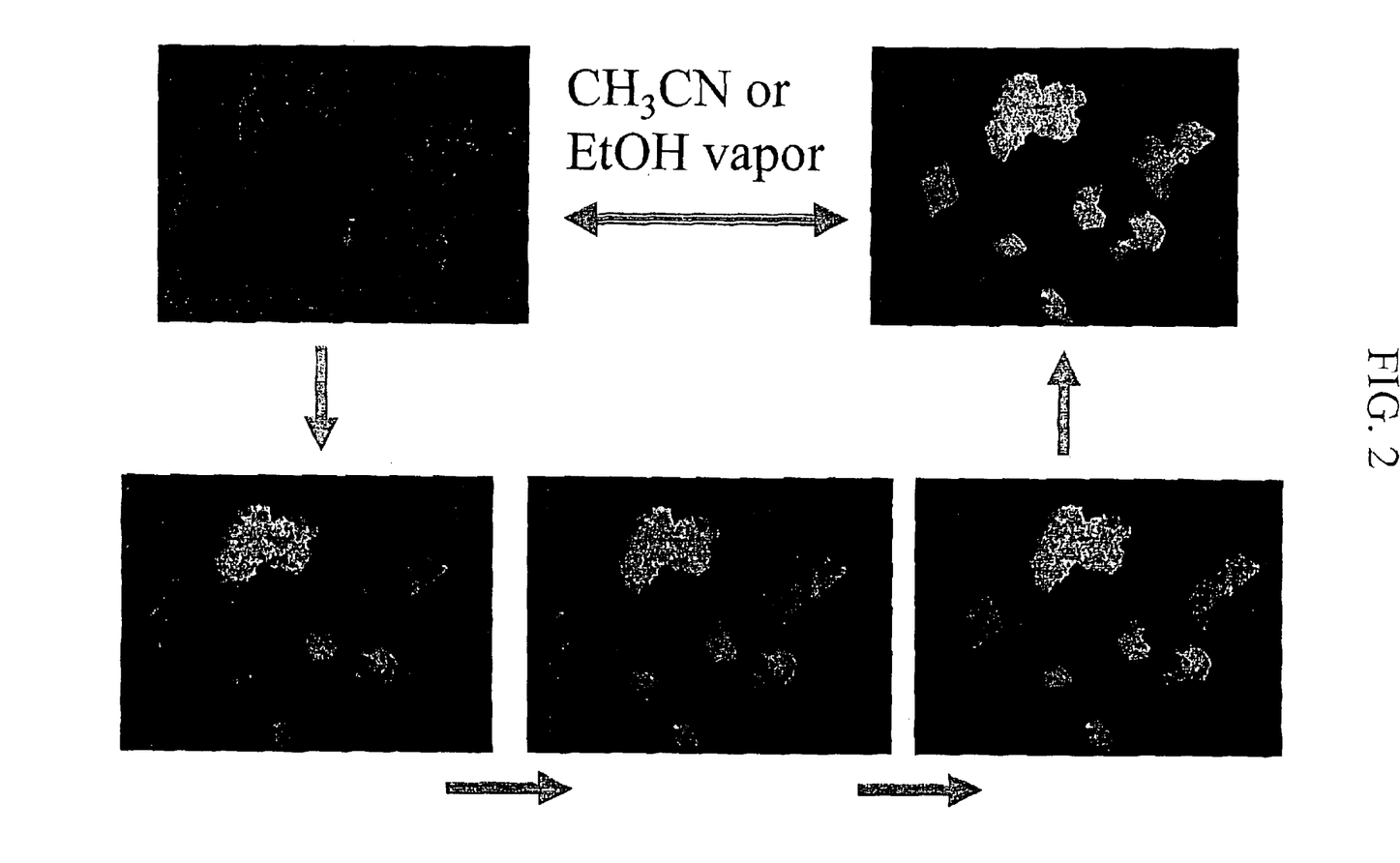
FIG. 2 is luminescence images of crystals of the syn isomer of [Pt$_2$(pyt)$_2$(bpy)$_2$](PF$_6$)$_2$ illustrating vapochromic effects.
Figure 3:
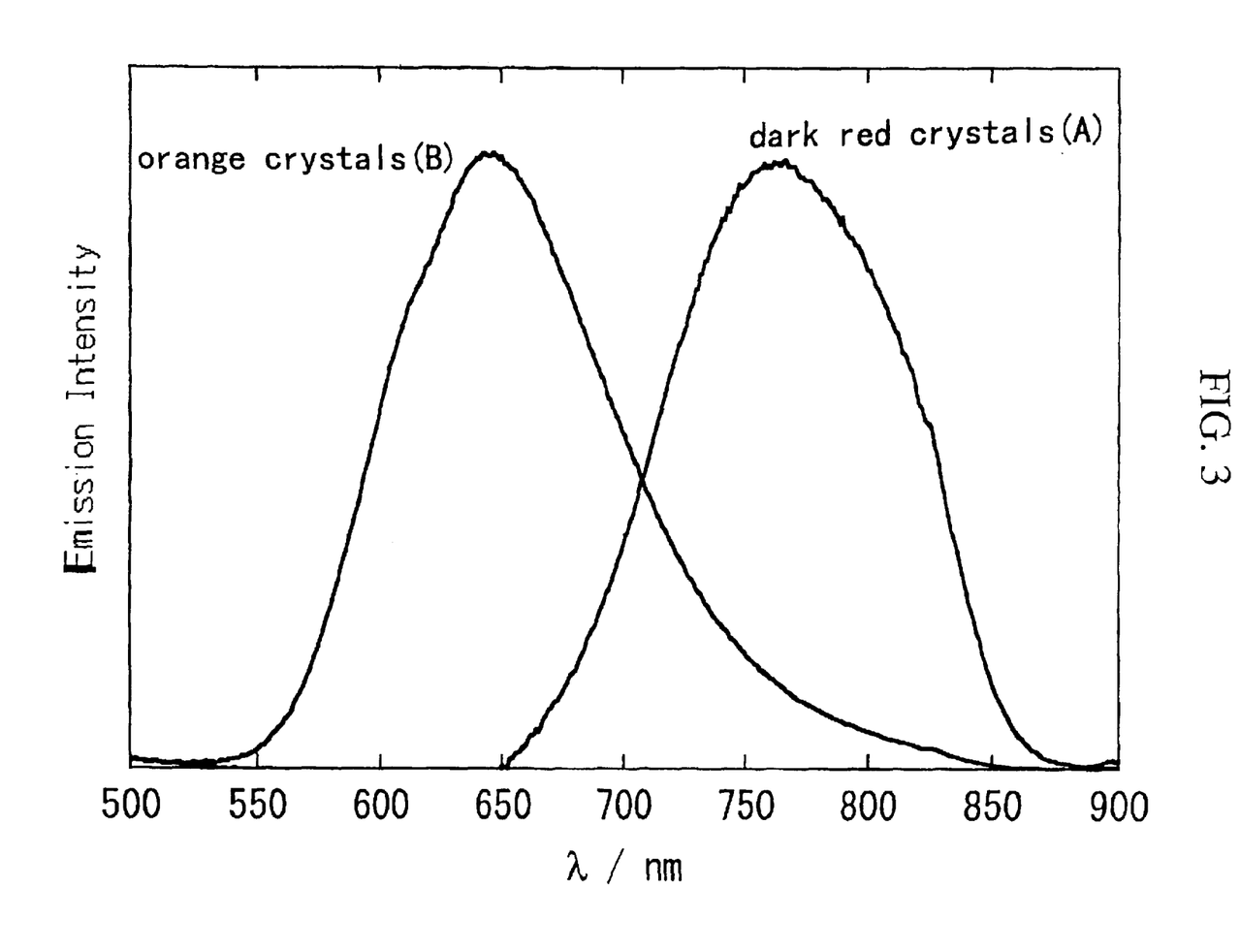
FIG. 3 shows luminescent spectra at room temperature: A) red-black crystal, B) red orange crystal of [Pt$_2$(pyt)$_2$(bpy)$_2$](PF$_6$)$_2$.

Also, the greatest characteristic of this binuclear complex is to exhibit a remarkable luminescence change in concert with the color change. FIG. 2 shows the process of the change from the dark red crystal to red by desorbing the solvent molecules which was observed approximately every one hour by a fluorescent microscopy (excitation at 380 nm). The initial dark red crystal is intense black. In FIG. 2, an outline of the crystal is faintly seen, which is because a marginal portion has already changed to red in color. This crystal was observed to gradually become lighter with the elapse of time as shown in the figure. When this red crystal was exposed to the vapor of alcohol, it reverted back to intense black in a moment of time. As a result of measuring the luminescent spectrum, it was demonstrated that the red crystal showed the luminescence maximum at 644 nm and the other dark red crystal showed the spectrum having the luminescence maximum at 766 nm (FIG. 3).

That is, the dark red crystal does not emit any light but emits invisible light at near infrared region. Since the luminescent states of this complex crystal by organic vapors change across the visible and near infrared regions, the change visually looks like on-off of the luminescence. This nature indicates that organic materials can be easily detected visually in quality as well as by spectrometry in quantity.

Figure 4:
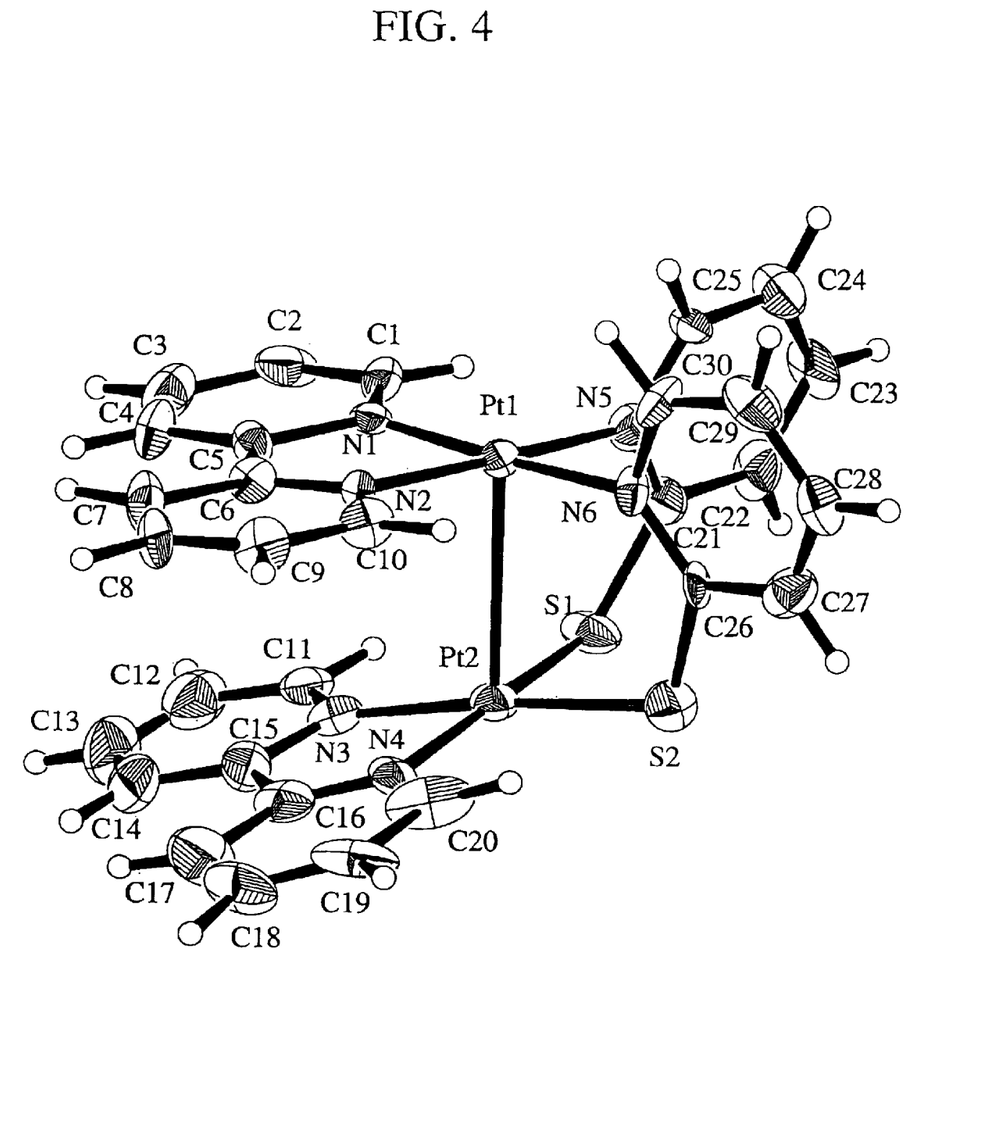
FIG. 4 shows the structure of [Pt$_2$(pyt)$_2$(bpy)$_2$]$^{2+}$ in [Pt$_2$(pyt)$_2$(bpy)$_2$](PF$_6$)$_2$ red block crystal. -Syn type structure.
Figure 5:
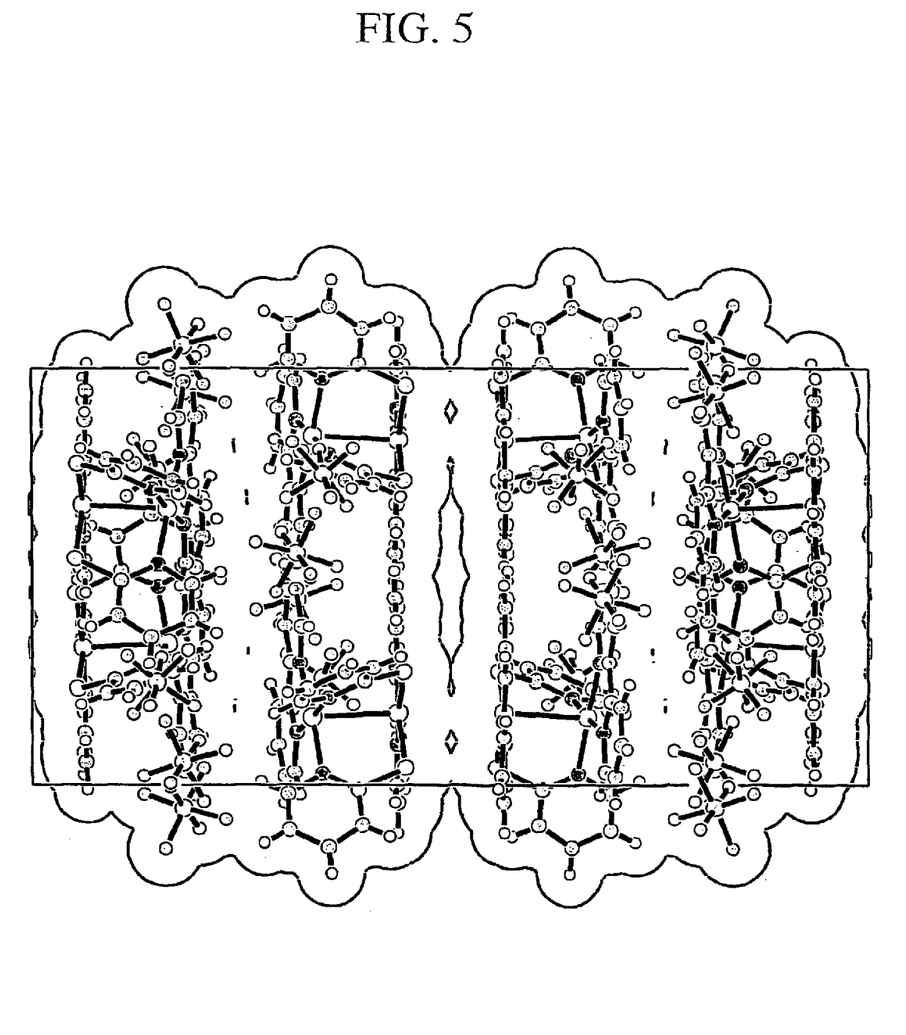
FIG. 5 shows the packing structure of [Pt$_2$(pyt)$_2$(bpy)$_2$](PF$_6$)$_2$ red block crystal.

Crystal Structure of [Pt$_2$(pyt)$_2$(bpy)$_2$](PF$_6$)$_2$ Red Black Polyhedral Crystal As a result of X-ray structural analysis of the dark red crystal, it was found that the structure of this binuclear complex is the syn type structure as shown in FIG. 4. That is, in this complex, both of the two pyridine thiolate anions of the bridging ligand are coordinated to the upper and lower platinum ions in the forms of N—S. Therefore in this case, two platinum ions are in the different environments. The packing in the crystal (figure viewed from the C axis direction) is shown in FIG. 5. It is shown that the platinum at the site where the binuclear complex is coordinated at S are orderly arranged with face to face and there are spaces between the complexes. In the actual dark red crystal, acetonitrile of the solvent molecule appears to be contained here, but the precise location could not be determined by the X ray analysis. However, from this crystal structure, it is found that when the acetonitrile molecules enter into these spaces (channels), then the crystal becomes black whereas when they get out, then it becomes red.

Figure 6:
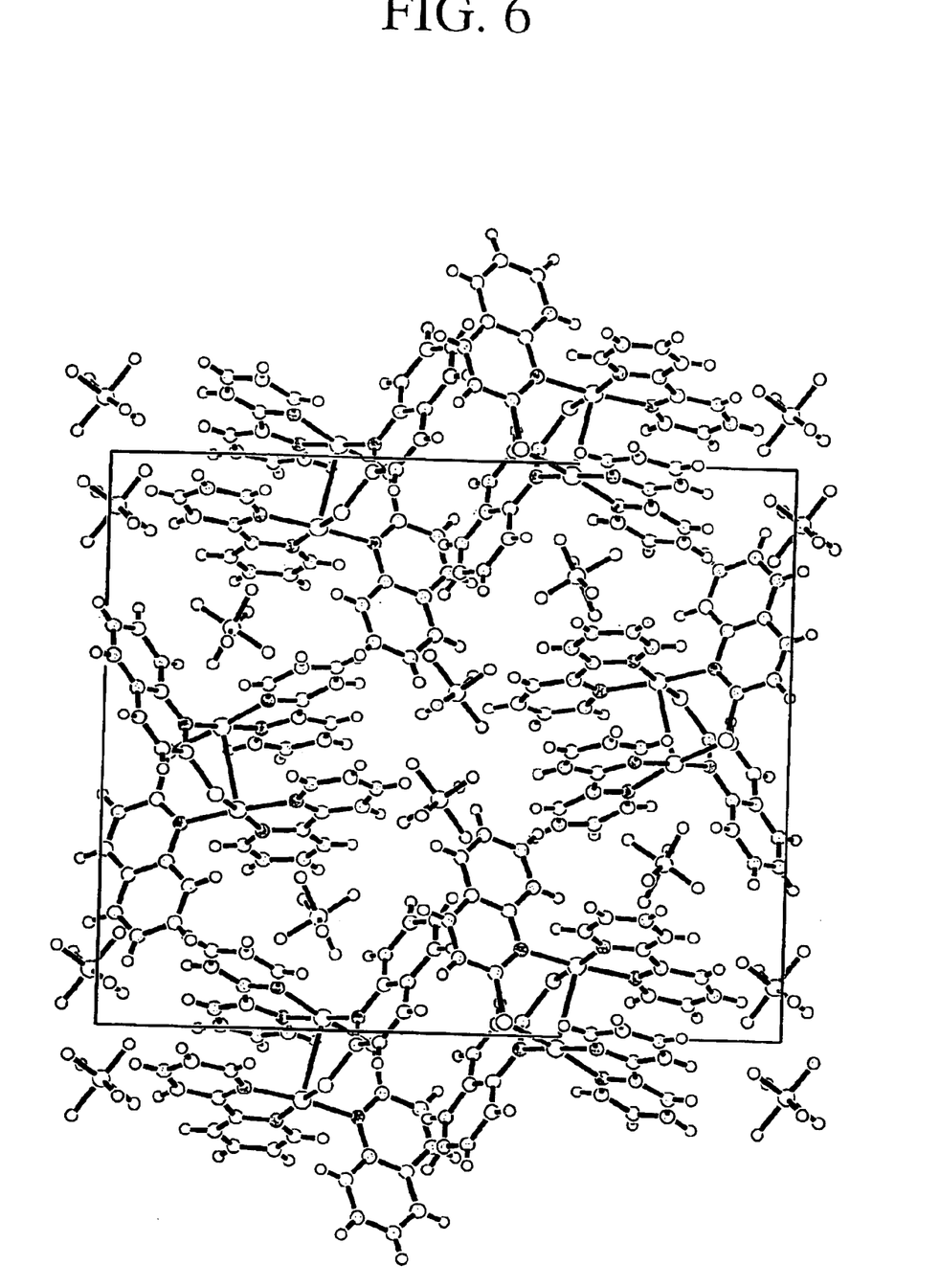
FIG. 6 shows the packing structure of [Pt$_2$(2-qlt)$_2$(bpy)$_2$](PF$_6$)$_2$ orange crystal.
Figure 7:
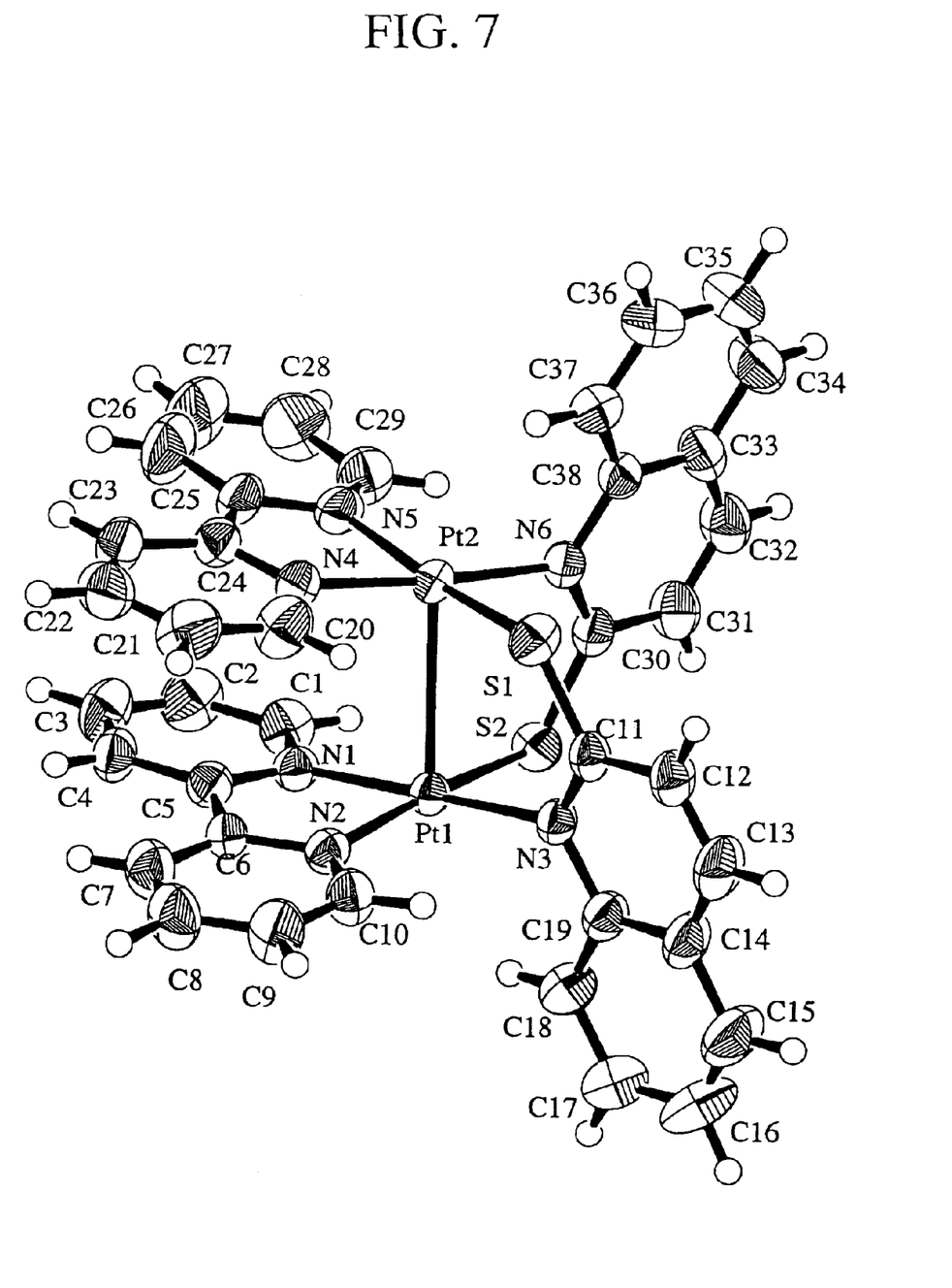
FIG. 7 shows the structure of [Pt$_2$(2-qlt)$_2$(bpy)$_2$]$^{2+}$ in [Pt$_2$(2-qlt)$_2$(bpy)$_2$](PF$_6$)$_2$ orange crystal. -Anti type structure.

For comparison, in FIG. 6, shown is the packing of the anti-type quinoline-2-thiolate bridging binuclear complex [$Pt_2(2\text{-}qlt)_2(bpy)_2$]($PF_6$)$_2$ orange crystal which does not cause vapochromism, obtained from the result of X ray structural analysis. In this case, there is no channel structure, and it is the structure where direct interaction between binuclear complexes is completely ruled out. Additionally, as is shown in FIG. 7, it was found that [$Pt_2(2\text{-}qlt)_2(bpy)_2$]$^{2+}$ in [$Pt_2(2\text{-}qlt)_2(bpy)_2$]($PF_6$)$_2$ orange crystal had the anti type structure.

Industrial Applicability

The binuclear platinum (II) complex of the invention reversibly absorbs and desorbs the vapor of organic molecules such as acetonitrile and ethanol, and changes between dark-red and light-red in color and simultaneously causes the change of luminescence between near-infrared/red and red. Therefore, taking advantage such a nature, visually effective on-off of the luminescence or electric changes can be observed. The binuclear platinum (II) complex of the invention can be used as highly sensitive sensors or environmental proves based on these properties.

What is claimed is:

1. A binuclear platinum (II) complex represented by the following formula:

[$Pt_2(L)_2(bpy)_2$]$X_2$ or [$Pt_2(L)_2(bpy)_2$]Y (wherein L represents a bridging ligand, as well as bpy represents 2,2'-bipyndine, X and Y represent a monovalent anion and bivalent anion, respectively), characterized in that both of the two bridging ligands(L) are syn types wherein the ligand is arranged with one side platinum ion by S and with the other side platinum ion by N.

2. The binuclear platinum (II) complex according to claim 1, characterized in that X is selected from the group consisting of $PF_6^-$, $ClO_4^-$; $BF_4^-$; $Cl^-$ and $Br^-$.

3. The binuclear platinum (II) complex according to claim 1, characterized in that Y is $SO_4^{2-}$.

4. The binuclear platinum (II) complex according to claim 1, characterized in that the bridging ligand is a thiolate anion derived from a heterocyclic aromatic compound.

5. The binuclear platinum (II) complex according to claim 1, characterized in that the bridging ligand is selected from the group consisting of pyridine-2-thiolate anion (pyt), qionoline-2-thiolate anion (2-qlt) or quinoline-8-thiolate anion (8-qlt).

6. The binuclear platinum (II) complex according to claim 1, characterized in that two bridging ligands are the same compounds.

7. The binuclear platinum (II) complex according to claim 1, characterized in that two bridging ligands are different compounds one another.

8. The binuclear platinum (II) complex according to claim 1, characterized in that the bridging ligand is pyridine-2-thiolate anion (pyt).

9. The binuclear platinum (II) complex according to claim 1, characterized in that the bridging ligand is qionoline-2-thiolate anion (2-qlt).

10. The binuclear platinum (II) complex according to claim 1, characterized in that the bridging ligand is quinoline-8-thiolate anion (8-qlt).

11. A method for producing the binuclear platinum (II) complex according to claim 1, comprised by adding [$PtCl_2$(bpy)$_2$] and equivalent bridging ligand (L) to water, heating the suspension, filtrating the impurity, subsequently adding an excess salt compound containing X or Y to the resultant solution to generate precipitate, obtaining the precipitate by filtration and recrystallizing from an organic solvent.

12. A method for producing the binuclear platinum (II) complex according to claim 1, comprised by adding [$PtCl_2$(bpy)$_2$] and equivalent bridging ligand (L) to water, heating the suspension, filtrating the impurity, subsequently adding an excess of $NH_4PF_6$ to the resultant solution to generate precipitate, obtaining the precipitate by filtration and recrystallizing from an organic solvent.

13. An organic molecule detection sensor comprising the binuclear platinum (II) complex according to claim 1.

14. The detection sensor according to claim 13, wherein an organic molecule is alcohol.

15. The detection sensor according to claim 13, wherein an organic molecule is acetonitrile.

16. An organic molecule vapor monitor apparatus comprising the detection sensor according to claim 13.

17. A method for detecting volatile organic molecules in the environment by taking advantage of color change of the binuclear platinum (II) complex according to claim 13.

18. A method for detecting volatile organic molecules in the environment by taking advantage of luminescent change of the binuclear platinum (II) complex according to claim 13.

* * * * *